United States Patent [19]

Castner

[11] 4,060,468
[45] Nov. 29, 1977

[54] OLEFIN METATHESIS PROCESS AND CATALYST THEREFOR

[75] Inventor: Kenneth F. Castner, Akron, Ohio

[73] Assignee: The Goodyear Tire & Rubber Company, Akron, Ohio

[21] Appl. No.: 729,315

[22] Filed: Oct. 4, 1976

[51] Int. Cl.$^2$ .................... B01J 1/10; B01J 23/16; C07C 3/10; C07F 2/46
[52] U.S. Cl. .................. 204/158 R; 204/159.24; 204/162 R; 260/683 D; 252/447
[58] Field of Search .......... 204/158 R, 162 R, 159.24; 96/115 P; 252/447; 260/683 D

[56] References Cited

U.S. PATENT DOCUMENTS

| | | | |
|---|---|---|---|
| 3,836,444 | 9/1974 | Codet et al. | 204/159.24 |
| 3,878,074 | 4/1975 | Reichenbacher et al. | 204/162 R |
| 3,956,178 | 5/1976 | Greco et al. | 260/683 D |

*Primary Examiner*—Howard S. Williams
*Attorney, Agent, or Firm*—F. W. Brunner; J. Y. Clowney

[57] ABSTRACT

There is disclosed a method for preparing a catalyst useful for olefin metathesis comprising a mixture of a salt of a metal selected from tungsten, molybdenum, rhenium and tantalum, an oxygenated organic compound selected from the group represented by the formula:

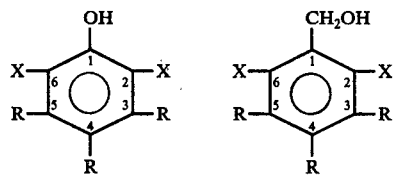

said mixture being exposed to ultraviolet radiation to give approximately 0.4 kilowatt hours per mole of the metal salt.

A process of olefin metathesis utilizing this catalyst is also disclosed.

8 Claims, No Drawings

OLEFIN METATHESIS PROCESS AND CATALYST THEREFOR

This invention is directed to a novel catalyst composition and its employment in chemical processes involving the olefin metathesis reaction. Specifically, the invention relates to certain metathesis catalysts which have their activity promoted photochemically, using ultraviolet (U.V.) radication and to methods of making these catalysts.

Olefin metathesis is a general name used to describe a class of reactions involving unsaturated compounds. Alternate names also used to describe the same class of reactions are olefin disproportionation and olefin dismutation. Specifically, olefin metathesis is a bond re-organization reaction that proceeds by a transalkylidenation pathway, wherein unsaturated reactants having at least one non-aromatic carbon-to-carbon double bond, undergo either intermolecular or intramolecular net cleavage and reformation of said double bonds.

Characteristic to olefin metathesis is the fact that, in the course of transformation of reactants to products, the total number and type of chemical bonds remain essentially unchanged. A general equation commonly used to illustrate olefin metathesis of acyclic unsaturated substrates is:

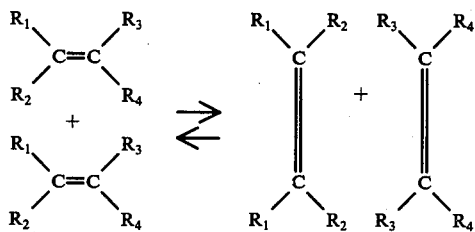

where $R_1$, $R_2$, $R_3$ and $R_4$ may be at least one member of the group consisting of alkyl, aryl, alkaryl, arylalkyl, cycloalkyl, radicals and hydrogen.

A variety of cycloolefin substrates may undergo ring-opening polymerization and copolymerization by olefin metathesis to yield polymeric materials.

For a detailed description of useful olefin metathesis processes, and the corresponding catalytic systems that promote said processes, reference is made to the following literature citations:

1. Catal. Rev., 3, 37 (1969),
2. Acc. Chem. Res., 5, 127 (1972),
3. Chem. Soc. Rev., 4, 1955 (1975)

and references cited therein.

With no exceptions, all of the disclosed catalysts that are capable of promoting the olefin metathesis reaction do possess at least one component which is a transition metal derivative; said derivative being either an oxide, a salt, or a coordination compound of certain metals belonging to Group IVa, Va, VIa, VIIa or VIII of the Periodic Table of Elements; with tungsten, molybdenum and rhenium as the most widely employed. THe aforementioned transition metal derivatives are often employed in combinations with a variety of co-catalysts. Hence, it is convenient to further classify metathesis catalysts into two major categories: (a) catalyst systems that employ at least one component, which is organometallic, in addition to the above mentioned transition metal derivative, and (b) systems that do not involve any organometallics as components of the metathesis catalyst, for instance tungsten oxide on alumina or silica support. The organometallic compounds used in category (a) are derived from certain metals of Groups Ia, IIa, IIb, IIIb and IVb of the Periodic Table of Elements. The term organometallic, as used herein, is understood to define compounds that possess at least one alkyl or aryl moiety which is bonded directly to the metal via a covalent or semi-ionic bond.

The catalyst system employed in this invention differs from those described above in several different aspects. One aspect is that the catalyst system is a two component system such as a salt of a metal selected from the group consisting of tungsten, molybdenum, rhenium and tantalum. However, the (B) component of the two component system differs in that it is not an organometallic compound but, instead, is an oxygenated organic ring compound possessing both an OH or hydroxyl functional group and also halogen or alkyl groups.

Therefore, the catalyst system of the present invention comprises (A) a salt of a metal selected from the group of tungsten, molybdenum, rhenium and tantalum, and (B) an oxygenated organic compound possessing both a hydroxyl group (OH) and a halogen represented by chlorine, bromine and iodine or an alkyl group such as t-butyl and isopropyl. An optional component (C) may be also employed, said component (C) being molecular oxygen. To obtain an efficient metathesis catalyst in accordance with this invention, the aforementioned components (A) and (B) and optional (C) in the proper proportions are activated photochemically by exposure to ultraviolet (U.V.) radiation. The time of exposure to U.V. is variable as it depends on the intensity and the wave length of the U.V. source, the total concentration of the catalyst, the thickness of the reaction cell, the specific catalyst component employed and the specific unsaturated olefinic reactants to be polymerized.

The minimum amount of ultraviolet radiation required to activate the catalyst components to give an active catalyst is approximately 0.4 killowatt hours per mole of $WCl_6$ in the catalyst system (non-monochromatic light with a Lambda max = 3000 A — λ max = 3000).

Representative of the salts of component (A) are $WCl_6$, $WCl_5$, $WCl_4$, $WBr_5$, $WOCl_4$, $WO_2CL_2$, $WOBr_4$.

Representative of the oxygenated organic (B) component are those selected from the group represented by the formula:

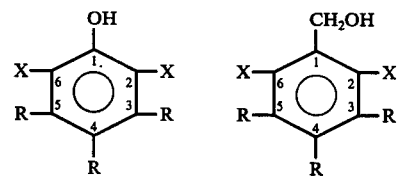

X is selected from Cl, Br, I, methyl isopropyl, t-butyl or t-hexyl group; R is selected from H, Cl, Br, I, alkyl aryl, arylalkyl, alkaryl and cycloalkyl. It is preferred that X be Cl, Br, I, isopropyl, t-butyl or t-hexyl.

Representative of such compounds are 2-chloro-4,6-dimethylphenol, 2,6-dichlorophenol, 2,6-dibromophenol, 2,6-diisopropylphenol, 2,3,6-trichlorophenol, 2,4,5,6-tetrabromophenol, 2,3,5,6-tetrachlorophenol, 2,3,4,5,6-pentachloro- or pentabromophenol, 2,6-dichloro-4-methylphenol, 2,6-dibromo-4-methylphenol, 2,6-dichloro-3,4-dimethylphenol, 2,6-dichlorobenzylalcohol, 2,6-dibromobenzyl alcohol, 2,6-diidobenzyl alcohol, 2,6-diisopropylphenol, 2-chloro6-methylphenol, 2,6-di-t-butyl-p-cresol, 2,6-di-t-hexylphenol, and the like.

To obtain an efficient metathesis catalyst according to this invention, the aforementioned components A and B, at properly chosen proportions, are activated photochemically by exposure to U.V. radiation. The time of exposure to U.V. is variable; as it depends on the intensity and the wave length of the U.V. source, the total concentration of the catalyst, the thickness of the reaction cell, the specific catalyst combination employed, and the specific unsaturated olefinic reactant used. The optimum exposure time for a given set of reaction conditions can be readily established by one skilled in the art.

Several procedures can be followed in carrying out the photochemical activation of the catalyst, and these are all within the scope of the present invention.

1. The cycloolefinic or olefinic reactant, in solution or in neat form, is charged into a reaction vessel with component A, followed by component B of the catalyst, and then exposed to the U.V. radiation source for the desired period of time. The operation is carried out under an inert atmosphere of nitrogen or argon.

2. A preformed solution of components A and B of the catalyst is prepared under inert atmosphere conditions. Low boiling and gaseous reaction byproducts of A and B components, e.g., HCl, can be removed by sparging the solution with a dry inert gas, like nitrogen. The preformed catalyst solution is then added totally or in part, into a vessel containing the olefinic reactant in neat or solution, and the whole reaction mixture exposed to the U.V. radiation source for the desired period of time. Inert reaction conditions are maintained as in (1).

3. A procedure similar to (1) except that component B of the catalyst is introduced into the reaction mixture during the exposure to the U.V. irradiation step.

4. A procedure similar to (1) except that component A of the catalyst is introduced into the reacting mixture during the exposure to the U.V. irradiation step.

5. A procedure wherein a preformed solution of components A and B, prepared as described in (2), is exposed to the U.V. radiation step and the olefinic reactant is introduced during, or immediately after, said exposure to the U.V. radiation.

Of all the procedures, (5) is preferred as a more active catalyst system results.

In carrying out metathesis reactions using any of the procedures described above, an excessive exposure of the system to air and moisture is to be avoided, as these generally cause deactivation of the catalyst. Nevertheless, it was discovered that controlled amounts of oxygen, when introduced diliberately before, during or immediately after the exposure to the U.V. radiation step, are beneficial to the catalyst systems described heretofore. As shown elsewhere in the specification, in the absence of deliberately added oxygen a substantial induction period, occurring after the radiation step and before the start of the actual metathesis reaction, is experienced. By a careful addition of controlled amounts of oxygen, henceforth considered as component C of the catalyst system, the induction period is shortened significantly. Hence, the reduction of the induction period by incorporation of component C which is oxygen into the process causes a decrease of the overall reaction time.

It is understood that procedures (1) to (5) for the photochemical activation of the catalyst as described above, can all be modified to include the addition of a third catalyst component (C), namely, molecular oxygen, before, during and/or immediately after the radiation step, and this modification is within the scope of the present invention.

Any part of the catalytic process of this invention can be carried out over a wide temperature range from about $-70°$ C. and lower to about 200° C. and higher, but generally, temperatures in the range of $-30°$ C. to 70° C. are suitable, with about 0° C. to about 50° C. being more suitable for this reaction. It is within the scope of this invention to conduct the photochemical activation of the catalyst by U.V. irradiation at a set temperature, and pursue the actual metathesis reaction at the same or at a different temperature.

In carrying out the olefin metathesis reaction by any of the procedures disclosed in the present specification, pressures under one atmosphere or higher than one atmosphere can be employed. However, it was found that the reaction pressure can conveniently be set at about one atmosphere. When gaseous materials are involved in a specific case, it is advisable to employ some pressure in order to ensure supply of reactants from the gas to the liquid phase where the metathesis-active catalyst is present.

The olefin metathesis reaction of this invention may be carried out in either neat or in the presence of a solvent. If a solvent is to be used, an inert solvent that does not deactivate the catalyst should be employed. Convenient solvents are aliphatic, aromatic or cycloaliphatic hydrocarbons, as well as chlorinated aromatic and chlorinated aliphatic solvents. Examples are: hexane, pentane, petroleum ether, benzene, toluene, chlorobenzene, methylene chloride, chloroform carbon tetrachloride.

Wave lengths useful for activation of the catalyst combinations of the present invention are not critical, and they cover essentially the complete range of the ultraviolet spectrum; that is, between 1900 A and 3800 A. Varied sources of non-monochromatic U.V. radiation with wave length (maximum) of 2438 A, 3000 A, and 3500 A have been tried and found effective to different degrees in promoting metathesis reactions with certain catalyst combinations as described in the present specification. As has been indicated, the minimum amount of ultraviolet radiation (non-monochromatic light with $\lambda$ max = 3000 A) required to activate the catalyst components is approximately 0.4 kilowatt hours per mole of the metal salt of tungsten, molybdenum, rhenium or tantalum. There seems to be no upper limit to the U.V. irradiation.

The amount of catalyst employed in the metathesis reactions of this invention may be varied over wide concentrations and has not been found to be critical. Of course, a catalytic amount of the catalyst must be employed. The optimum amount of catalyst depends upon a number of factors such as radiation time and intensity of U.V. source, reaction temperature, type of olefinic reactants to be metathesized, purity of reactants, desired rates of reaction to reach completion, and others. Those skilled in the art will readily determine the optimum catalytic levels for a given set of specific reaction variables. The reaction can be conducted at a level of component A, namely, the transition metal derivative, wherein for every one mole of olefinic reactants to be metathesized, about 0.001 mole component A is employed.

The molar relationship between the two catalyst components A and B as previously defined, may vary substantially depending on the specific composition of said components. In broad terms, the A/B mole ratio may be about 0.25.1 to about 15/1, with a more preferred molar ratio of A/B of about 0.5/1 to about 8/1, and a still more preferred molar ratio of A/B of about 0.75/1 to about 2/1. The molar ratio of A/C may be about 50/1 to about 0.25/1, with a more preferred molar ratio of A/C of about 10/1 to about 0.5/1, and still more preferred molar ratio of A/C of about 6/1 to about 2/1.

Unsaturated substances that may undergo metathesis in accordance with this invention are numerous. These may comprise: (a) acyclic olefinic compounds; (b) acyclic nonconjugated di-, tri- and multiolefins; (c) cyclic olefins possessing at least one carbon-to-carbon double bond; (d) multicyclic unsaturated compounds which may be substituted by certain functional groups; (e) unsaturated polymeric materials. Acyclic olefins that undergo metathesis correspond to the formula:

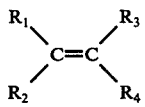

wherein $R_1$, $R_2$, $R_3$ and $R_4$ may be at least one member of the hydrocarbyl group consisting of alkyl, aryl, alkaryl, arylalkyl, cycloalkyl radicals and hydrogen; and these are subdivided into terminal olefins ($R_3$ and $R_4$ = H, $R_1$ and $R_2$ may be H or other hydrocarbyl radicals); disubstituted olefins ($R_1$ and $R_3$ = H, $R_2$ and $R_4$ are hydrocarbyl radicals); trisubstituted olefins ($R_1$ = H; $R_2$, $R_3$ and $R_4$ are hydrocarbyl radicals); tetrasubstituted olefins ($R_1$, $R_2$, $R_3$ and $R_4$ are hydrocarbyl radicals). Representative members of this group are: ethylene, propylene, 1-butene, 1-pentene, styrene, vinylcyclohexene, isobutylene, alpha-methylstyrene and the like; 2-butene, 2-pentene, 2-hexene, 3-hexene, stilbene, 2-, 3- and 4-octene and the like; 2-isobutyl-2-butene and tetramethyl ethylene.

Nonconjugated acyclic di-, tri- and multiolefins that may undergo metathesis by the process of this invention correspond to the formula:

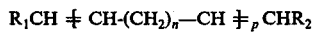

wherein $n \geq 2$ and $p = 1, 2, 3 \ldots$; $R_1$ and $R_2$ are hydrocarbyl radicals or hydrogen. Representative examples are: 1,4-hexadiene, 1,4-heptadiene, 1,5-heptadiene, 1,7-octadiene, 2,6-octadiene, 1,5,9-decatriene and the like.

Cyclic olefins that may undergo metathesis by the process of this invention include compounds selected from the group consisting of:

A. alicyclic compounds corresponding to the formula:

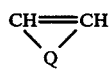

wherein:
1. Q is a fragment which comprises a sequence of at least 5 carbon atoms situated in linear succession between the methylidene carbons which constitute the double bond;
2. the carbon atoms in the linear succession of Q may be interconnected by both carbon-carbon single bonds and carbon-carbon double bonds;
3. any of the carbon atoms in the linear succession of Q may be substituted by at least one member from the group of alkyl, aryl, aralkyl, alkaryl, cycloalkyl, bicycloalkyl and bicycloalkenyl radicals;
4. any of said carbon atoms in the linear succession of Q may be constituents of aromatic rings, alicyclic rings and chlorinated alicyclic rings; and
5. said alicyclic unsaturated hydrocarbon contains no non-aromatic conjugated double bonds; and B. alicyclic compounds corresponding to the formula:

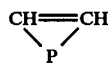

wherein:
1. P is a fragment which comprises a sequence of at least 2 and not more than 3 carbon atoms situated in linear succession between the methylidene carbons which constitute the double bond;
2. the carbon atoms in linear succession of P are connected by carbon-to-carbon single bonds;
3. any of the carbons in the linear succession of P may be substituted by at least one substituent member from the group of alkyl, aryl, aralkyl, alkaryl, cycloalkyl, bicycloalkyl and bicycloalkenyl radicals;
4. any of said carbons in linear succession of P may be constituents of aromatic rings, alicyclic rings, and chlorinated alicyclic rings, and
5. said alicyclic unsaturated hydrocarbon compound contains no non-aromatic conjugated double bonds.

Representative examples are: cyclobutene, cyclopentene, cycloheptene, cyclooctene, 1,5-cyclooctadiene, cyclododecene, 1,5,9-cyclododecatriene and 1-methyl-1,5-cyclooctadiene.

Multicyclic unsaturated compounds which may undergo metathesis according to the process of this invention are: dicyclo[2.2.1]hept-2-ene (norbornene), dicyclo[2.2.1]hepta-2,5-diene (norbornadiene), dicyclo[4.3.0]nona-3.7-diene, and dicyclo]2.2.2.]oct-2-ene. In addition, multicyclic unsaturated compounds which are substituted by certain functional groups may also undergo metathesis by the process of this invention. These include hexachlorocyclopentadiene-cyclooctadiene adduct having the formula:

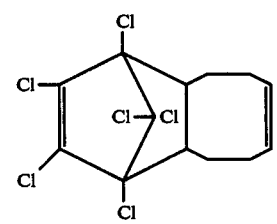

and substituted norbornenes of the general formula:

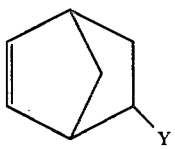

where Y represents Cl, CN, COOR, OCOR and pyridyl.

Polymeric materials which may undergo metathesis according to this process are of the general formula:

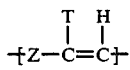

wherein:
A. T is
1. hydrogen; or
2. a substituent corresponding to the formula

where D is any member of the group: alkyl, aryl, aralkyl, alkaryl, cycloalkyl, bicycloalkyl, bicycloalkenyl and hydrogen; and
B. Z represents a structure having at least two carbon atoms and any of the said Z carbons may be
1. interconnected by single or double bonds;
2. substituted by one or more members of the group alkyl, aryl, aralkyl, alkaryl, cycloalkyl, bicycloalkyl and bicycloalkenyl;
3. constituents of aromatic, alicyclic or chlorinated alicyclic rings; and
4. said polymeric material contains no nonaromatic conjugated double bonds.

It is within the scope of this invention to carry out the metathesis reaction on mixtures of two or more of the aforementioned unsaturated reactants. For example: (1) the cross-metathesis of two acyclic olefins; (2) the metathesis of an acyclic with a cycloolefin; (3) the reaction of a substituted cycloolefin with a non-substituted cycloolefin in the presence or absence of acyclic olefins; (4) the cross-metathesis reaction of a multicyclic, substituted cycloolefin with an acyclic olefin; (5) the cross-metathesis of two polymeric materials; and others.

The practice of this invention is illustrated by reference to the following examples which are intended to be representative rather than restrictive of its scope.

EXAMPLE I

Pentene-2 (mixed isomers), was purified by refluxing over $CaH_2$ (under nitrogen) for 8 hours followed by distillation. The distilled olefin was made up as a 10% by volume solution in commercial grade cyclohexane and passed through a $SiO_2/Al_2O_3$ drying column under nitrogen atmosphere. The column-passed material was transferred to 16-ounce screw-cap bottles fitted with self-sealing gaskets and Teflon liners. 0.025 M $WCl_6$ and 0.025 M pentachlorophenol (PCP) were made up in dry cyclohexane. Reaction tubes (25 × 150 mm quartz or Pyrex test tubes) were conditioned by heating in a 140° C. oven for at least 24 hours. A magnetic stirring bar was added to the reaction tube and the tube stoppered with a serum septum. The tube was cooled while purging with nitrogen, employing 22 gauge needles as inlet and outlet tubes. After 20 minutes of purging, the outlet needle was removed followed by the inlet needle, leading to pressurization of the reaction tube.

Nine (9) ml of 2-pentene solution was transferred to the reaction tube by syringe. Then, 0.5 ml of 0.025 M pentachlorophenol was added followed by 0.5 ml of 0.025 M of $WCl_6$. The tube was then placed in a photochemical reactor (Rayonet, 3000 A employed in all the examples below) equipped with a magnetic stirrer and irradiated for a period to give approximately 1.6 KWH per mole initial $WCl_6$ at ambient temperature and constant stirring. This tube was stored at room temperature in the dark for about 18 hours without any further agitation. The reaction was quenched with 0.25 ml of distilled water. Product analysis was carried out by gas chromatography. The results are shown in Table 1.

EXAMPLE II

Ingredients and procedure the same as in Example I, with the exception that 2,6-dichlorophenol (2,6-DCP) was used in place of PCP. Results are shown in Table 1.

EXAMPLE III

Ingredients and procedure the same as in Example I, with the exception that 2,6-dibromophenol (2,6-DBP) was used in place of PCP. Results are shown in Table 1.

EXAMPLE IV

Same as Example I with the exception that 40 ml of pentene-2 was employed and 2 ml each of 0.025 M $WCl_6$ and 0.025 M PCP. Samples were taken by syringe at various time intervals and injected into screw-cap vials containing about 0.1 ml distilled water. Results are reported in Table 1.

EXAMPLE V

Same as Example IV with the exception that after irradiation, 0.20 ml oxygen ($O_2/W = 0.18$) was added and the contents stirred an additional 5 minutes. Results are reported in Table 1.

EXAMPLE VI

Same as Example V with the exception that after irradiation 0.39 ml oxygen ($O_2/W = 0.35$) was added. Results are reported in Table 1.

EXAMPLE VII

Ingredients and procedure the same as Example I but with the exception that the PCP and $WCl_6$ were preformed. Thus, to a 0.025 m $WCl_6$ solution in cyclohexane, sufficient PCP was added to give PCP/W of 1/1. The solution was shaken for about 3 hours and the evolved HCl was sparged off by bubbling dry nitrogen through the solution. Cyclohexane was added to replace that last in the sparging operation. This preformed solution was then used in place of the $WCl_6$ and PCP solutions. Results are reported in Table 1.

Table 1

| Results of Pentene-2 Metathesis Employing $WCl_6$/Modifier/UV | | | | |
| --- | --- | --- | --- | --- |
| Pentene-2 | → | Butene-2 + Hexene-3 | | |
| 50% | ← | 25% | 25% | |
| Ex | Phenolic Modifier | $O_2/W$ | Induction Time(min) | Time to 90% Conversion (min) | Ultimate Conv (%) |
| I | PCP | 0 | — | — | 100[b] |
| II | 2,6-DCP | 0 | — | — | 100[b] |
| III | 2,6-DBP | 0 | — | — | 100[b] |

Table 1-continued
Results of Pentene-2 Metathesis Employing
WCl₆/Modifier/UV

Pentene-2 → Butene-2 + Hexene-3
50% ← 25% 25%

| Ex | Phenolic Modifier | O₂/W | Induction Time(min) | Time to 90% Conversion (min) | Ultimate Conv (%) |
|---|---|---|---|---|---|
| IV | PCP | 0 | 290 | 343 | 100[b] |
| V | PCP | 0.18 | 160 | 191 | 100[b] |
| VI | PCP | 0.35 | 25 | 70 | 100[b] |
| VII | PCP[a] | 0 | — | — | 100[b] |

[a] preformed with WCl₆.
[b] Conversion % equilibrium.

EXAMPLE VIII 1,5-cyclooctadiene (COD) was made up as a 20% by volume solution in cyclohexane and passed through a SiO₂/Al₂O₃ column under nitrogen atmosphere. The dried monomer solution was collected in a 16 oz. screw-cap bottle fitted with self-sealing gasket and Teflon liner.

Reaction tubes were prepared as described in Example I. Forty ml monomer solution was transferred by syringe into the reaction tube. Two ml 0.025 M WCl₆/PCP was preformed and prepared as described in Example VII was added and the tube irradiated for 20 minutes to give 2.4 KWH/mole of WCl₆ at ambient temperature with constant stirring and then stored in the dark at room temperature for about 18 hours. The polymer was coagulated with methanol and vacuum dried for 24 hours yielding 1.7 gram which is 25% yield of high molecular weight rubber.

EXAMPLE IX

Purification and polymerization technique identical with Example VIII, except employed dicyclopentadiene (DCPD) in place of COD. Reaction yielded 0.94 gram polymer which is 12% yield.

EXAMPLE X

Purification and polymerization technique identical with Example VIII, except employed cyclopentene (CP) in place of COD. Reaction yielded 0.68 gram high molecular weight rubber.

Table 2
Results of Polymerization Studies Employing
Preformed WCl₆/PCP/UV

| Example | Cycloolefin | Yield (g) | Yield (%) |
|---|---|---|---|
| VIII | COD | 1.7 | 25 |
| IX | DCPD | 0.94 | 12 |
| X | CP | 0.68 | 36 |

EXAMPLE XI

COD and cyclohexane were purified by passing through a silica gel/alumina column under nitrogen atmosphere. Seven ml cyclohexane was added to the reaction tube, followed by 1.5 ml 0.025 M WCl₆ and 1.5 ml. 0.025 M 2,6-dibromophenol. The solution was irradiated to give 2.4 KWH/mole of initial WCl₆. After irradiation, 10 M COD was added. After 18 hours the polymer was coagulated with methanol and vacuum dried, yielding 5.33 g (61% yield) of high molecular weight polymer.

EXAMPLE XII

Purification and polymerization technique identical with Example XI, except added 2 ml cyclohexane and 5 ml COD before irradiation. After irradiation, added 5 ml cyclohexane and 5 ml COD (giving the same tungsten concentration during and after irradiation as employed in Example XI). The polymerization yielded 1.05 grams (12% yield) of high molecular weight polymer.

While certain representative embodiments and details have been shown for the purpose of illustrating the invention, it will be apparent to those skilled in this art that various changes and modifications may be made therein without departing from the spirit or scope of the invention.

What is claimed is:

1. The method of preparing a catalyst useful for olefin metathesis which comprises mixing (A) a salt selected from the group consisting of WCl₆, WCl₅, WCl₄, WBr₅, WOCl₄, WO₂Cl₂, and WOBr₄, and (B) an oxygenated organic compound selected from the group represented by the formula:

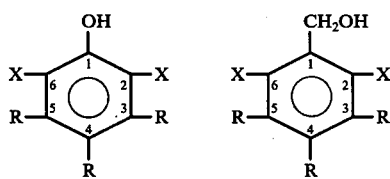

X is selected from Cl, Br, I, methyl, isopropyl or t-butyl group; R is selected from H, Cl, Br, I, alkyl, aryl, arylalkyl, alkaryl and cycloalkyl; and subsequently exposing said mixture of (A) and (B) to ultraviolet irradiation for at least long enough to give approximately 0.4 KWH per mole of the metal salt of tungsten.

2. The method according to claim 1 in which the salt of (A) is tungsten hexachloride and the oxygenated organic compound is selected from the group of 2,6-dichlorophenol, 2,6-dibromophenol, 2,6-isopropylphenol, 2,6-diiodophenol, 2,3,6-trichlorophenol, 2,4,5,6-tetrachlorophenol, 2,6-diisopropylphenol and 2,6-di-t-butyl-p-cresol.

3. The method according to claim 1 in which (C) molecular oxygen is included in the catalyst.

4. The method according to claim 2 in which (C) molecular oxygen is included in the catalyst.

5. An olefin metathesis process which comprises subjecting at least one member selected from the group consisting of olefins and cycloolefins to a catalyst comprising mixing (A) a salt selected from the group consisting of WCl₆, WCl₅, WCl 4, WBr₅, WOCl₄, WO₂Cl₂, and WOBr₄, and (B) an oxygenated organic compound selected from the group represented by the formula:

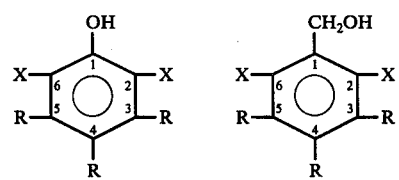

X is selected from Cl, Br, I, methyl, isopropyl or t-butyl group; R is selected from H, Cl, Br, I, alkyl, aryl, arylalkyl, alkaryl, and cycloalkyl; and subsequently exposing said mixture of (A) and (B) to ultraviolet irradiation for at least that which is equivalent to approximately 0.4 kilowatt hours per mole of the initial amount of the salt of tungsten.

6. The process according to claim 5 in which the salt of (A) is tungsten hexachloride and the oxygenated organic compound is selected from the group of 2,6-dichlorophenol, 2,6-dibromophenol, 2,6-isopropylphenol, 2,6-diiodophenol, 2,3,6-trichlorophenol, 2,4,5,6-tetrachlorophenol, 2,6-diisopropylphenol and 2,6-di-t-butyl-p-cresol.

7. The process according to claim 5 in which (C) molecular oxygen is included in the catalyst.

8. The process according to claim 6 in which (C) molecular oxygen is included in the catalyst.

* * * * *